United States Patent
Galvan

(12) 
(10) Patent No.: US 8,337,819 B2
(45) Date of Patent: Dec. 25, 2012

(54) PHARMACEUTICAL COMPOSITION FOR THE ORAL HYGIENE, THE TREATMENT OF THE PERIODONTAL ILLNESSES AND THE HALITOSIS

(76) Inventor: Tomas Bernardo Galvan, Santiago (CL)

(*) Notice: Subject to any disclaimer, the term of this patent is extended or adjusted under 35 U.S.C. 154(b) by 685 days.

(21) Appl. No.: 11/532,443

(22) Filed: Sep. 15, 2006

(65) Prior Publication Data

US 2008/0299051 A1  Dec. 4, 2008

(51) Int. Cl.
*A61Q 11/00* (2006.01)
*A61K 31/05* (2006.01)
*A61K 31/055* (2006.01)
*A61K 31/327* (2006.01)

(52) U.S. Cl. ........... 424/53; 424/49; 514/714; 514/724; 514/730; 514/731; 514/737; 514/900

(58) Field of Classification Search ............ 424/49, 424/53; 514/714, 724, 730, 731, 737, 900
See application file for complete search history.

(56) References Cited

U.S. PATENT DOCUMENTS

| | | | |
|---|---|---|---|
| 4,900,721 A * | 2/1990 | Bansemir et al. | 514/25 |
| 5,942,211 A * | 8/1999 | Harper et al. | 424/49 |
| 6,010,993 A * | 1/2000 | Romano et al. | 510/309 |
| 6,375,933 B1 | 4/2002 | Subramanyam et al. | |
| 2002/0136698 A1 | 9/2002 | Bhakoo et al. | |
| 2003/0162838 A1* | 8/2003 | Yumioka et al. | 514/625 |

FOREIGN PATENT DOCUMENTS

| | | |
|---|---|---|
| EP | 1351658 B1 | 10/2003 |
| WO | WO02055643 | 7/2002 |

OTHER PUBLICATIONS

Jana et al.—"Estudio Clinico Comparativo entre Colutorio de p-clorofenol y peroxido de hidrogeno con Colutorio de Clorhexidina al 0.12% en el Crecimiento de Placa Microbiana y Gingivitis" (Jana et al., Rev. Clin. Periodoncia Implanol. Rehabil. Oral, vol. 3(2); 65-68 2010) 5 Pages (Spanish Language).

Jana et al.- "Comparative clinical study between p-chlorophenol and hydrogen peroxide mouthwash with chlorhexidine 0.12% mouthwash in the growth of microbial plaque and gingivitis" (Jana et al., Rev. Clin. Periodoncia Implanol. Rehabil. Oral, vol. 3(2); 65-68 2010) 7 pages (English Translation).

* cited by examiner

*Primary Examiner* — Lezah Roberts
(74) *Attorney, Agent, or Firm* — Hasse & Nesbitt LLC; Daniel F. Nesbitt

(57) ABSTRACT

The invention is a pharmaceutical composition for the oral hygiene for the treatment of the periodontal illnesses and the Halitosis. It consists of a mixture 0.01 to 5 g of Hydrogen Peroxide; 0.001 to 0.5 g of Eugenol: 0.001 to 0.5 g of Permonochlorophenol; 0.001 to 0.3 g of Camphor; 10 to 40 g of Maltitol; 0.01 to 0.1 g of coloring matter; 0.1 to 1 g of appetizing substance and enough quantity of demineralized water to complete 100 g of oral pharmaceutical preparation.

8 Claims, No Drawings

PHARMACEUTICAL COMPOSITION FOR THE ORAL HYGIENE, THE TREATMENT OF THE PERIODONTAL ILLNESSES AND THE HALITOSIS

RELATED APPLICATIONS

Not Applicable

FIELD OF THE INVENTION

Not Applicable

BACKGROUND OF THE INVENTION

In the field of the oral hygiene and of the preventive dentistry, a wide range of products exists in form of toothpastes and oral mouthwash, whose main function is to care and maintain the oral hygiene. Many of them are made up of gluconato of chlorhexidine of sodium. With the use of these substances, in addition to a correct daily brushing and the guidance or professional treatment, pursuing to maintain a good state of oral health in an appropriate way.

Unfortunately in the scope of the periodontal illnesses (gingivitis in its diverse grades) the products that exist in our markets have not been effective for the cure and the prevention of these illnesses. Many of these oral mouthwashes and toothpastes even try to base their effectiveness on the number of times to be used during the day, but good clinical results have not been achieved.

Examples to consider of well-known oral mouthwash in our country are Oral-B (M.R.) and Dento (M.R.). In both cases their active components are: Chloride of Cetilpiridinio and Floruro of Sodium. Other well-known collutories are: Halita (M.R.) whose active component is Gluconate of chlorhexidine; Plax (M.R.) made up of Fluoride of Sodium and Trichlosan; and Listerina (M.R.) with Methyl Salicylate and Timol.

In a revision of searching for patents by classification A61 K007/20 two applications in step were found, whose numbers are Ser. No. 09/753,854 and 01300336.3 from United States of America and from Europe, respectively, and whose composition is, in both cases, very different, from the pharmaceutical preparation that we present. On the other hand, in A61K7/26, revised in esp@cenet, just one pharmaceutical preparation was found made with Eugenol as the basic ingredient, but that corresponds to a cosmetic composition of essential oils to protect the skin.

SUMMARY OF THE INVENTION

A pharmaceutical composition for the oral hygiene, the treatment of the periodontal illnesses and the Halitosis, characterized because it consists of a mixture 0.01 to 5 g of Hydrogen Peroxide; 0.001 to 0.5 g of Eugenol: 0.001 to 0.5 g of Permonochlorophenol; 0.001 to 0.3 g of Camphor; 10 to 40 g of Maltitol; 0.01 to 0.1 g of coloring matter; 0.1 to 1 g of appetizing substance and enough quantity of demineralized water to complete 100 g of oral pharmaceutical preparation.

The Halitosis and the periodontal illnesses have their origin in diverse germs that inhabit the oral cavity. These germs are fundamentally anaerobes and other aerobes. The halitosis is a very unfavorable condition which has high incidence in the population. This condition affects very deeply the self-esteem and many times the normal performance of people in its social and affective environment.

The Halitosis, the bad or offensive breath that emanates from the oral cavity, can have a local, extra oral or remote origin. The properly sources, such local or oral ones, which are sought to be corrected with this pharmaceutical preparation, can be:

1. The retention of odoriferous particles, coming from foods on the teeth and among them.
2. Saburral tongue.
3. Gingivitis in its diverse grades.
4. States of dehydration and/or oral dryness.
5. Cavities.
6. Artificial dentures.
7. Smoker breath.
8. Intraoral surgical wounds.
9. Chronic periodontal illnesses with periodontal bags.
10. Abundant tartar stuck in the dental pieces.
11. Systemic illness.

To correct these problems of oral health we propose the use, inform of oral mouthwash, toothpaste or other forms of a pharmaceutical preparation that contains—as an active principle—Hydrogen Peroxide, Eugenol, Permonochlorophenol and Camphor, and that next we describe and specify in percentage weight-weight.

DETAILED DESCRIPTION OF THE INVENTION

The Hydrogen Peroxide, in concentrations of 0.001 to 0.5%, is enough effective to destroy of the anaerobic bacteria. It also makes it safe in regard to not causing tisular damage in the normal soft tissues of the oral and pharyngeal mucosa.

The mechanism of action of this pharmaceutical preparation, in the first place is due to the presence and effervescence of the Hydrogen Peroxide inside the mouth, when it is used. Its action and activation is favored by the Catalasa, a salivary enzyme. With this effervescence, the liberation of oxygen from the Peroxide destroys the strict anaerobic microorganisms. In the same way, this action eliminates the smell caused by the destruction of the odoriferous volatile organic molecules. The Peroxide in this pharmaceutical compound can also serve as an agent which removes spots from the organic pigments stuck on the dental structures. It can also be effective in the destruction of the bacterial plaque, helping to its elimination and avoiding its adherence on the teeth. It also serves as a therapeutic agent of post surgical wounds.

The Permonochlorophenol is an antiseptic and antimicrobial compound of a disinfectant action, in a concentration of between 0.01 and 0.05%, helps to strengthen the germicide action of the product.

The Eugenol, is an essential oil derived from the tent oil in concentration of between 0.01 and 0.05%. It also produces an antiseptic, antibacterial and disinfectant effect, acting, therefore, as other helper for the effectiveness of this mouthwash.

The Camphor, present in concentrations of 0.001 to 0.3% exercises an action ant inflammatory in the oral mucosa, in the periodontal tissues and in gums. It also acts as an antiseptic, and helps to extend the antibacterial effect of the product as well.

The remaining non active ingredients are: a synthetic sweetening agent, an appetizing substance, a coloring matter and demineralized water.

Maltitol has been used as a sweetening entity in this mouthwash, in ranges of 10 to 40%. Maltitol is a polyalcohol that, besides its nature of alcohol, it helps to preserve and to stabilize the activity of the Peroxide. Another particularity is that it is not cariogenic and capable for diabetic people, because in the event of involuntary ingestion, it doesn't elevate the glycemia levels in the patients.

As an appetizing substance different types of flavors have been incorporated, such as: anisette, mint, orange, cherry, lime-lemon, in quantities of a 0.1 to 1%.

The coloring matter can be red 40, brilliant blue, egg yellow, mint green and those that are added in ranges from 0.01 to 0.1%.

Finally, it contains demineralized water in quantity enough to complete 100 g of the product (100%).

Next an example to prepare 100 g. of the product is presented:
TABLE-US-00001 Hydrogen Peroxide 0.1 g. (0.1% 0 0.33 Vol.) Eugenol 0.01 g. (0.01%) Permonochlorophenol 0.006 g. (0.006%) Camphor 0.004 g. (0.004%) Liquid appetizing substance 0.8 g. (0.8%) Coloring matter 0.05 g. (0.05%) Maltitol 20 g. (20%) Demineralized water csp 100 g.

This pharmaceutical preparation, being used three times a day and keeping it in the mouth during one minute, produces good effects as to decrease the gingival inflammation the prevention of the neo formation of the bacterial plaque. It also fights against the Halitosis. These effects have been able to be clinically tested in 28 patients, examined and supervised by a professional odontologist.

What is claimed is:

1. A composition for oral hygiene for the treatment of periodontal illnesses and halitosis consisting by weight, in demineralized water, of a mixture of 0.01 to 0.1% hydrogen peroxide; 0.001 to 0.5% eugenol; 0.001 to 0.006% p-chlorophenol; 0.001 to 0.3% camphor; 10 to 40% maltitol; 0.01 to 0.1% coloring matter; and 0.1 to 1% flavor.

2. The composition for oral hygiene for the treatment of periodontal illnesses and halitosis according to claim 1, consisting of 0.01% eugenol.

3. The composition for oral hygiene for the treatment of periodontal illnesses and halitosis according to claim 1, consisting of 0.004% camphor.

4. The composition for oral hygiene for the treatment of periodontal illnesses and halitosis according to claim 1, consisting of 20% maltitol.

5. The composition for oral hygiene for the treatment of periodontal illnesses and halitosis according to claim 1, consisting of 0.8% flavor.

6. The composition for oral hygiene for the treatment of periodontal illnesses and halitosis according to claim 1, consisting of 0.1% coloring matter.

7. The composition for oral hygiene for the treatment of periodontal illnesses and halitosis according to claim 1, where the flavor is selected from the group consisting of lime-lemon, cherry, orange, mint, anisette, and mixtures thereof.

8. The composition for oral hygiene for the treatment of periodontal illnesses and halitosis according to claim 1, where the coloring matter is selected from the group consisting of red 40, egg yellow, mint green, brilliant blue, and mixtures thereof.

* * * * *

UNITED STATES PATENT AND TRADEMARK OFFICE
CERTIFICATE OF CORRECTION

PATENT NO. : 8,337,819 B2  
APPLICATION NO. : 11/532443  
DATED : December 25, 2012  
INVENTOR(S) : Tomas Bernardo Galvan Page 1 of 1

It is certified that error appears in the above-identified patent and that said Letters Patent is hereby corrected as shown below:

In the Claims

Claim 6, Column 4, Line 17, delete "0.1%". Insert --0.01%--.

Signed and Sealed this  
Twenty-first Day of July, 2020

Andrei Iancu  
*Director of the United States Patent and Trademark Office*